(12) United States Patent
Pullar

(10) Patent No.: US 9,943,471 B2
(45) Date of Patent: Apr. 17, 2018

(54) BETA-2-ADRENERGIC RECEPTOR AGONIST FOR IMPROVING SKIN SCAR COLOUR MATCHING

(71) Applicant: UNIVERSITY OF LEICESTER, Leicester (GB)

(72) Inventor: Christine Elaine Pullar, Leicester (GB)

(73) Assignee: UNIVERSITY OF LEICESTER, Leicester (GB)

( * ) Notice: Subject to any disclaimer, the term of this patent is extended or adjusted under 35 U.S.C. 154(b) by 198 days.

(21) Appl. No.: 14/772,895

(22) PCT Filed: Mar. 7, 2014

(86) PCT No.: PCT/GB2014/050686
§ 371 (c)(1),
(2) Date: Sep. 4, 2015

(87) PCT Pub. No.: WO2014/135896
PCT Pub. Date: Sep. 12, 2014

(65) Prior Publication Data
US 2016/0008247 A1 Jan. 14, 2016

(30) Foreign Application Priority Data
Mar. 8, 2013 (GB) .................................. 1304234.6

(51) Int. Cl.
| | | |
|---|---|---|
| A61K 8/41 | (2006.01) | |
| A61Q 17/04 | (2006.01) | |
| A61Q 19/02 | (2006.01) | |
| A61K 31/00 | (2006.01) | |
| A61K 31/137 | (2006.01) | |
| A61K 8/49 | (2006.01) | |

(52) U.S. Cl.
CPC .............. *A61K 8/41* (2013.01); *A61K 8/4926* (2013.01); *A61K 31/00* (2013.01); *A61K 31/137* (2013.01); *A61Q 17/04* (2013.01); *A61Q 19/02* (2013.01); *A61K 2800/78* (2013.01)

(58) Field of Classification Search
None
See application file for complete search history.

(56) References Cited

U.S. PATENT DOCUMENTS

| 5,958,432 A | 9/1999 | Breton et al. |
|---|---|---|
| 2006/0235048 A1 | 10/2006 | Weidner |
| 2011/0201691 A1* | 8/2011 | Pullar .................. A61K 31/138 514/653 |

FOREIGN PATENT DOCUMENTS

| EP | 1719507 | 11/2006 |
|---|---|---|
| EP | 1764081 | 3/2007 |
| EP | 2529724 | 12/2012 |
| JP | 2011506413 | 3/2011 |
| WO | WO 01/94319 | 12/2001 |
| WO | WO 03/097073 | 11/2003 |
| WO | WO 2006/027579 | 3/2006 |
| WO | WO 2006/108176 | 10/2006 |
| WO | WO 2007/137204 | 11/2007 |
| WO | WO 2009/074796 | 6/2009 |
| WO | WO 2009/118541 | 10/2009 |
| WO | WO 2012/170695 | 12/2013 |

OTHER PUBLICATIONS

Davis et al. "Postinflammatory Hyperpigmentation".*
Halder et al., "Acne in ethnic skin", *Dermatol Clin.*, 21: 609-615, 2003.
Montagna and Yun, "The skin of the domestic pig", *The Journal of investigative dermatology*, 42: 11-71, 1964.
"The Role of Adrenergic Best Receptors for Skin Pigmentation", P&G beauty & grooming report on FC17-10, dated 2011.
"Ventolin Inhaler", Data Sheet, dated Nov. 18, 2011.
Akutsu et al., "Transforming growth factor βs are upregulated in the rat masseter muscle hypertrophied by clenbuterol, a $\beta_2$ adrenergic agonist", *Br J Pharmacol.*, 147: 412-421, 2006.
Baker, "The selectivity of β-adrenoceptor agonists at human $\beta_1$-, $\beta_2$- and $\beta_3$-adrenoceptors", *British Journal of Pharmacology*, 160: 1048-1061, 2010.
Beausang et al., "A new quantitative scale for clinical scar assessment", Plastic & Reconstructive Surgery, 102: 1954-1961, 1998.
Coley and Alexis, "Managing common dermatoses in skin of color", *Seminars in cutaneous medicine and surgery*, 28: 63-70, 2009.
Draaijers et al., "The patient and observer scar assessment scale: a reliable and feasible tool for scar evaluation", *Plastic and reconstructive surgery*, 113: 1960-1965, 2004.
Eggleston et al. "A controlled trial of long-term bronchodilator therapy in Cystic Fibrosis", *Chest*, 99: 1088-1092, 1991.

(Continued)

*Primary Examiner* — Robert A Wax
*Assistant Examiner* — Danah Al-Awadi
(74) *Attorney, Agent, or Firm* — Parker Highlander PLLC

(57) ABSTRACT

A method for improving skin scar color matching, for example reducing scar hyperpigmentation, the method comprising administering a therapeutically effective amount of an agent, which positively modulates β2-adrenergic receptor conformation, or receptor activity, or activation thereof, to a subject in need thereof. The subject typically is in need of improving skin scar color matching, for example reducing scar hyperpigmentation, because the subject has or is at risk of hyperpigmentation. The subject typically is selected as being at risk of hyperpigmentation on the basis of one or more of the following factors: • the subject has previously developed hyperpigmentation of a scar • the subject tans readily on exposure to sunshine or ultraviolet (UV) radiation, rather than burning • the subject has a non-Caucasian racial origin • the subject's skin color (for example in an area that is not tanned) is considered to be darker than that typical of a naturally fair-haired Caucasian person. The subject may be selected as being at risk of hyperpigmentation because they are at least predominantly of Chinese, black African, Asian or Southern European racial origin, and/or if their skin type can be assessed under the Fitzpatrick Scale as Type III, IV, V or VI.

12 Claims, 7 Drawing Sheets

(56) References Cited

OTHER PUBLICATIONS

Figure 1:
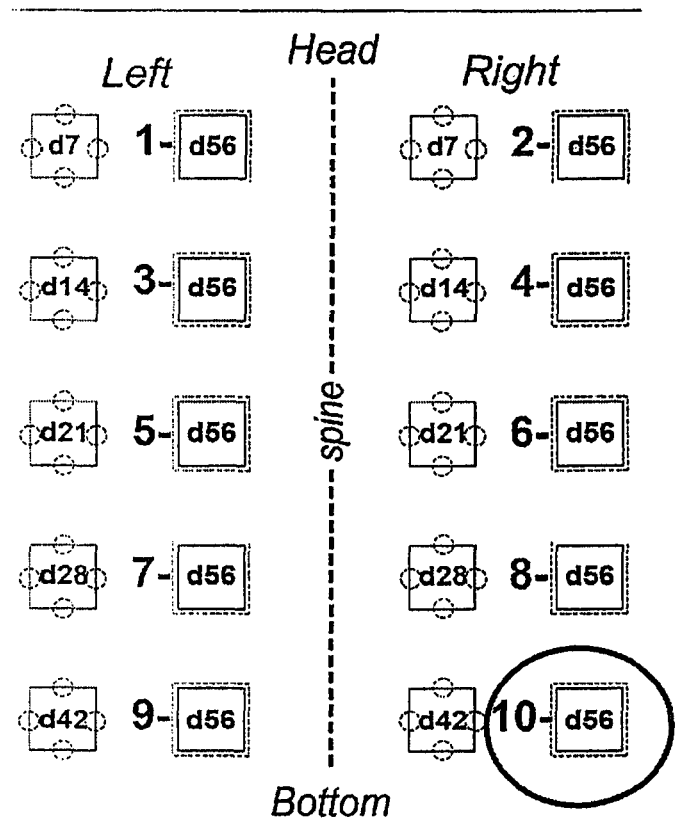

Elwood et al., "Pigmentation and skin reaction to sun as risk factors for cutaneous melanoma: Western Canada Melanoma Study", *British Medical Journal*, 288: 99-102, 1984.
Fitzpatrick, "The validity and practicality of sun-reactive skin types I through IV", *Archives of dermatology*, 124: 869-871, 1988.
Galko et al., "Cellular and genetic analysis of wound healing in Drosophila larvae", *PLoS biology*, 2: E239, 2004.
Gallant et al., "Molecular, histologic, and gross phenotype of skin wound healing in red Duroc pigs reveals an abnormal healing phenotype of hypercontracted, hyperpigmented scarring", *Wound Repair and Regeneration*, 12: 305-319, 2004.
Gallant-Behm and Hart, "Genetic analysis of skin wound healing and scarring in a porcine model", *Wound Repair and Regeneration*, 14: 46-54, 2006.
Gallant-Behm et al. "The mast cell stabilizer ketotifen prevents development of excessive wound contraction and fibrosis in red Duroc pigs", *Wound Repair and Regeneration*, 16: 226-233, 2008.
Gallant-Behm et al., "Genetic involvement in skin wound healing and scarring in domestic pigs: assessment of molecular expression patterns in (Yorkshire×Red×Duroc)×Yorkshire backcross animals", *The Journal of investigative dermatology*, 127: 233-244, 2007.
Gillbro et al., "Autocrine catecholamine biosynthesis and the $\beta_2$-adrenoceptor signal promote pigmentation in human epidermal melanocytes", *J Invest Dermatol*, 123: 346-353, 2004.
Gillbro et al., "The melanogenesis and mechanisms of skin-lightening agents—existing and new approaches", *International Journal of Cosmetic Science*, 33: 210-21, 2011.
Gurtner et al., "Improving cutaneous scar by controlling the mechanical environment", *Annals of surgery*, 254: 217-225, 2011.
Halder et al., "Ethnic skin disorders overview", *J Am Acad Dermatol.*, S143-S148, 2003.
Harunari et al., "Histology of the thick scar on the female, red Duroc pig: final similarities to human hypertrophic scar", *Burns*, 32: 669-677, 2006.
Hayward et al., "Animal models of wound contraction", in *Clinical and Experimental Approaches to Dermal and Epidermal Repair: Normal and Chronic Wounds*, Pub. Wiley-Liss, Inc., 1991. pp. 301-312.
Hutchings et al., "Pharmacokinetics and metabolism of salbutamol in premature labour", *Br J Clin Pharmacol*, 24: 69-75, 1987.
Johnson, "Molecular mechanisms of $\beta_2$-adrenergic receptor function, response, and regulation", *J Allergy Clin Immunol* 117: 18-24, 2006.
King et al., "Melanocytic lesions associated with dermatofibromas: a spectrum of lesions ranging from junctional nevus to malignant melanoma in situ", *Modern Pathology*, 18: 1043-1047, 2005.
Kobilka et al., "cDNA for the human $\beta_2$-adrenergic receptor: a protein with multiple membrane-spanning domains and encoded by a gene whose chromosomal location is shared with that of the receptor for platelet-derived growth factor", *PNAS* 84: 46-50, 1987.
Konda et al., "New horizons in treating disorders of hyperpigmentation in skin of color", *Seminars in cutaneous medicine and surgery* 31: 133-139, 2012.
Lear et al., "Risk factors for basal cell carcinoma in the UK: case-control study in 806 patients", *Journal of the Royal Society of Medicine* 90: 371-374, 1997.
Levesque et al., "Inflammation drives wound hyperpigmentation in zebrafish by recruiting pigment cells to sites of tissue damage", *Disease models & mechanisms* 6: 508-515, 2013.
Liang et al., "[Pathomorphological observation of the hypertrophic scar induced by injury to conical structure in female red Duroc pig]" *Chinese journal of burns* 22: 29-32, 2006. (English abstract).
Marles et al., "Tyrosine hydroxylase isoenzyme I is present in human melanosomes: a possible novel function in pigmentation", *Experimental Dermatology* 12: 61-70, 2003.
Meier and Nanney, "Emerging new drugs for scar reduction", *Expert Opinion on Emerging Drugs* 11: 39-47, 2006.
Morgan et al., "Pharmacokinetics of intravenous and oral salbutamol and its sulphate conjugate", *Br J Clin Pharmacol* 22: 587-593, 1986.
Mustoe, "Discussion—The patient and observer scar assessment scale: a reliable and feasible tool for scar evaluation", *Plastic and reconstructive surgery*, 113: 1966-1967, 2004.
Nieuweboer-Krobotova, "Hyperpigmentation: types, diagnostics and targeted treatment options", *Journal of the European Academy of Dermatology and Venereology* 27 Suppl 1: 2-4, 2013.
Osborne et al., "Application of genomics to breakthroughs in the cosmetic treatment of skin ageing and discoloration", *The British Journal of Dermatology* 166 Suppl: 2 16-19, 2012.
Pathac, "Preventative treatment of sun burn, dermatoheliosis, and skin cancer with sun protective agents", In: Fitzpatrick T, Eisen AZ, Wolff K, editor. Dermatology in general medicine. 4th edition ed. New York: McGraw-Hill Inc. pp. 1689-1717, 1993.
PCT International Search Report and Written Opinion issued in International Application No. PCT/GB2014/050686, dated Sep. 23, 2014.
Pullar and Isseroff, "$\beta_2$-adrenergic receptor activation delays dermal fibroblast-mediated contraction of collagen gels via a cAMP-dependent mechanism", *Wound Rep and Regen* 13: 405-411, 2005.
Pullar et al., "$\beta_2$-adrenergic receptor activation delays wound healing", *The FASEB Journal*, 20: 76-86, 2006.
Rasmussen et al., "Crystal structure of the human $\beta_2$ adrenergic G-protein-coupled receptor", *Nature* 450: 383-387, 2007.
Rohrbach et al., "[The melanocyte and the eye: a review with special emphasis on the cornea]", *Klinische Monatsblatter fur Augenheilkunde*, 229: 42-47, 2012. (English abstract).
Sina and Goldner, "Malignant melanoma and pigmented lesions: a diagnostic and management dilemma", *Southern Medical Journal*, 83: 1218-1223, 1990. (Abstract).
Sivamani et al., "An epinephrine-dependent mechanism for the control of UV-induced pigmentation", *The Journal of Investigative Dermatology* 129: 784-787, 2009.
Sullivan et al., "Rating the burn scar", Journal of Burn Care & Rehabilitation, 11(3): 256-260, 1990.
Sullivan et al., "The pig as a model for human wound healing", *Wound Repair Regen* 9: 66-76, 2001.
van der Wal et al., "Objective Color Measurements: Clinimetric Performance of Three Devices on Normal Skin and Scar Tissue", *Journal of burn care & research*, 2012.
Wang et al., "Zebrafish beta-adrenergic receptor mRNA expression and control of pigmentation", *Gene* 446: 18-27, 2009.
Yang et al., "Expression profiling of UVB response in melanocytes identifies a set of p53-target genes", *The Journal of Investigative Dermatology* 126: 2490-2506, 2006.
Zhu et al., "Review of the female Duroc/Yorkshire pig model of human fibroproliferative scarring", *Wound Repair Regen.*, 15(Suppl 1): S32-39, 2007.
Yang et al. "Abnormalities in the basement membrane structure promote basal. keratinocytes in the epidermis of hypertrophic scars to adopt a proliferative phenotype." *International journal of molecular medicine* 37.5 (2016): 1263-1273.

* cited by examiner

BETA-2-ADRENERGIC RECEPTOR AGONIST FOR IMPROVING SKIN SCAR COLOUR MATCHING

This application is a national phase application under 35 U.S.C. § 371 of International Application No. PCT/GB2014/050686, filed Mar. 7, 2014, which claims priority to United Kingdom Application No. 1304234.6, filed Mar. 8, 2013. The entire text of each of the above referenced disclosures is specifically incorporated herein by reference.

The present invention relates to pharmaceutical compositions, medicaments and methods of treatment for the improvement of skin scar colour match, for example reduction or treatment of scar hyperpigmentation.

Fibroblasts are involved in many processes within the body. Wound healing is a complex process requiring the combined activation of numerous processes including the modulation of fibroblast activity. During the wound healing process, dermal fibroblasts migrate to the wound bed where wound cell-secreted Transforming Growth Factor-1 (TGF-β1), matrix molecules (eg a fibronectin splice variant) and mechanical cues (ie matrix tension) initiate their differentiation into myofibroblasts. Myofibroblasts can be distinguished from dermal fibroblasts as they express smooth muscle α-actin, contain bundles of contractile microfilaments, and have extensive cell-to-matrix attachment sites. The myofibroblasts synthesise, deposit and remodel the extracellular matrix to form granulation tissue, and thereby contract the wound. The connective tissue that forms during the healing process is often fibrous in nature, and commonly forms into a connective tissue scar by a process known as fibrosis.

In the embryo, healing processes are activated and halted to regenerate tissue perfectly, and so scarring may not occur. However, in the adult, evolution has optimised wound healing processes to achieve wound closure quickly, minimising the risk of infection, but resulting in scar formation. Viewed macroscopically, scars may be depressed below the surface of the surrounding tissue, or elevated above the surface of the undamaged skin. Scars may be relatively darker coloured than the unwounded tissue (hyperpigmentation) or may have a paler colour (hypopigmentation) than their surroundings. Either hyperpigmented or hypopigmented scars constitute a readily apparent defect, and 100 million patients develop wound scars every year from elective operations, trauma, burn injuries and keloids. It has been shown that the appearance of a scar is one of the major factors contributing to the psychological impact of wounds upon the sufferer, and that these effects can remain long after the wound itself has healed.

WO 2006/108176 relates to β2 AR agonists and antagonists for modulating wound healing, wound contraction and/or epithelialization. Various uses of or observations on β2 AR agonists are disclosed in EP 1 719 507; WO 01/94319; WO 2007/137204; U.S. Pat. No. 5,958,432; WO 03/097073; WO 2006/027579; Eggleston et al (1991) *Chest* 99, 1088-1092; Barzon et al (1991) *Eur. Resp. J.* 19, 2307-2311; Skipsii et al (1991) *Terapevtiicheski Arkhiv* 63, 125-127; Pullar & Isseroff (2005) *Wound Rep. & Regen.* 13, 405-411; Pullar et al (2006) *FASEB J.* 20, 76-86; and Akutsu et al (2006) *Br. J. Pharmacol.* 147, 412-421.

WO 2009/118541 also relates to β2 AR agonists and antagonists for modulating fibroblast responses, for modulating the deposition of collagen or combating a fibrotic disorder, or for combating scarring.

The Fitzpatrick skin typing system was created in 1975 for predicting skin reactivity in oral methoxsalen (PUVA) photochemotherapy, a treatment for psoriasis [1]. Since then, the Fitzpatrick classification has been used world-wide to estimate the risk of basal cell carcinoma [2] and cutaneous malignant melanoma [3]. The interview-led or self-reporting skin-typing system relied on a questionnaire that the person used to grade their tendency to burn and ability to tan 24 hours and 7 days after the first un-protected sun exposure in early summer. Defined by Fitzpatrick, the initial sun exposure is 3 times the minimal erythema dose (MED), which is the UV dose that will elicit just perceptible erythema 24 hours after sun exposure [1]. This is equivalent to approximately 45 to 60 minutes of sun exposure in northern latitudes (20° to 45°) at noontime in May (90 mJ/cm$^2$).

There are 4 classifications for white skin (I through IV), brown skin is classified as type V and black skin and type VI [1, 4], see table 1 [1]. The skin type classification is composed of two components, the initial induced erythema or burn and the resulting pigmentation.

Table 1.

TABLE 1

| Skin Type | Erythema and tanning reactions to first sun exposure |
|---|---|
| I | Always burn, never tan |
| II | Usually burn, tan less than average (with difficulty) |
| III | Sometimes mild burn, tan average |
| IV | Rarely burn, tan more than average (with ease) |
| V | Brown-skinned persons |
| VI | Black-skinned persons |

The initial classification was based on responses in white skin and the scale was later improved to include classifications IV through VI for light brown, brown and black skin, respectively [4].

Skin colour is determined primarily by the type and amount of melanin in the skin. Pigment formation is highly complex. Melanocytes in cooperation with tyrosinase are responsible for the production and conversion of dopa to melanin and melanosomes containing the melanin pigment are taken-up by keratinocytes in the epidermis. Hyperpigmentation commonly occurs in Fitzpatrick skin types III to VI [5].

Measurements of scar colour are often part of scar evaluation, so vascularization (erythema/redness) and pigmentation (melanin) are routine outcome parameters (alongside other parameters) in scar research [6]. Scar colour can be assessed o subjectively using a scar assessment scale [7, 8, 9] (see below) or objectively using a measurement device, which can give a measure of hyperpigmentation. Melanin levels can be measured with the Mexameter (provides an erythema and melanin index based on the principle of narrow band spectrophotometry) or the DSM II Colourimeter (combines narrow band spectrophotometry with tristimulus reflectance coluorimetry) [6].

Wound hyperpigmentation can be observed in minor inflammatory dermatoses [5] acne scars [10] and in fibrotic wounds and lesions [11, 12, 13, 14, 15]. Hyperpigmentation is more commonly seen in people with dark complexion, Fitzpatrick skin types III to VI [5]. Indeed both hyperpigmentation and keloids occur at significantly higher rates in darkly pigmented persons [12, 13]. Hyperpigmentation is a major clinical problem that can cause considerable psychological distress [11, 12, 13, 14, 15]. There is also a body of evidence demonstrating a link between melanocytic lesions and melanoma [14, 16].

Current therapies for hyperpigmentation include removal of pigment in the superficial layer with acid peels, increase in melanosome transfer and down regulation of tyrosinase with Tretinoin, reduction of inflammation, melanocyte proliferation and secretion with corticosteroids and inhibition of tyrosinase and decreased melanogenesis with hydroquinone [5]. In addition, there are some new topical treatments such as soy, licorice, rucinol and resveratrol that are gaining popularity [15].

Currently, little is known about the cells and molecular signals that drive wound/scar hyperpigmentation. In zebrafish, inflammation in the wound appears to drive wound hyperpigmentation. Relatively large or chronic wounds trigger the recruitment of pigment cells, both undifferentiated precursors, melanoblasts and differentiated melanocytes, in both larvae and adults, leading to hyperpigmentation [17]. When the innate immune cells were depleted, melanocyte recruitment and the resulting hyperpigmentation did not occur, therefore inflammation was essential for wound hyperpigmentation in the zebrafish [17]. This document indicates that the zebrafish model may be useful as one in which to test possible therapeutic agents. In drosophila larvae, punch wounds are rapidly pigmented within hours of injury and the pigmentation might have a protective role against UV and invading bacteria [18].

Grando et al (2006) Journal of Investigative Dermatology (2006) 126, 1948-1965 notes that the specific β2-adrenoceptor agonist salbutamol enhances cAMP levels as well as receptor densities in association with increased melanogenesis (Gillbro et al., 2004) ["Autocrine catecholamine biosynthesis and the beta-adrenoceptor signal promote pigmentation in human epidermal melanocytes". J Invest Dermatol 123:346-53.] See also Raja K. Sivamani "An Epinephrine-Dependent Mechanism for the Control of UV-Induced Pigmentation" Journal of Investigative Dermatology (2009) 129, 784-787, which reports that Epinephrine increases melanin synthesis in melanocytes; and Wang et al Gene 446 (2009) 18-27 "Zebrafish β-adrenergic receptor mRNA expression and control of pigmentation", which notes that the authors cloned and characterized five zebrafish orthologs of β-AR genes representing homologs of three β-AR subtypes. Loss-of-function analysis revealed an important role for zebrafish adrb2a in the regulation of pigmentation, consistent with mammalian β2-AR.

Consistent with these finding, β2 AR antagonists are known as skin whitening agents. See, for example, J. M. Gillbro and M. J. Olsson "The melanogenesis and mechanisms of skin-lightening agents—existing and new approaches" International Journal of Cosmetic Science, 2011, 33, 210-221. See also review article Osborne et al (2012) B J Dermatol 166 (Suppl. 2), pp 16-19 "Application of genomics to breakthroughs in the cosmetic treatment of skin ageing and discoloration", which reports propigmentation roles for β adrenergic receptors.

The present inventors have surprisingly found that a β2 AR agonist is useful in improving skin scar colour matching, for example reducing scar hyperpigmentation. Thus, it is considered that a β2 AR agonist is useful in improving the similarity of pigmentation of the scar to the pigmentation of the surrounding skin.

A first aspect of the invention provides a method for improving skin scar colour matching, for example reducing scar hyperpigmentation, the method comprising administering a therapeutically effective amount of an agent, which positively modulates β2-adrenergic receptor conformation, or receptor activity, or activation thereof, to a subject in need thereof.

A second aspect of the invention provides an agent, which positively modulates β2-adrenergic receptor conformation, or receptor activity, or activation thereof, for use in improving skin scar colour matching, for example reducing scar hyperpigmentation, in a subject in need thereof.

A third aspect of the invention provides the use of an agent, which positively modulates β2-adrenergic receptor conformation, or receptor activity, or activation thereof, in the manufacture of a medicament for improving skin scar colour matching, for example reducing scar hyperpigmentation, in a subject in need thereof.

The invention may further or in addition have the effect of treating or aiding in preventing melanocytic lesions and/or melanoma in the subject.

Thus, a further representative aspect of the invention provides a method for treating or preventing melanocytic lesions and/or melanoma in a subject, the method comprising administering a therapeutically effective amount of an agent, which positively modulates β2-adrenergic receptor conformation, or receptor activity, or activation thereof, to a subject in need thereof.

The invention is considered to relate to a therapeutic intervention. In the alternative, the invention also provides a cosmetic treatment for improving skin scar colour matching, for example reducing scar hyperpigmentation, in a subject desirous thereof. Preferences are as set out in relation to other aspects of the invention.

Before the present invention it had not been appreciated that modulation of the β2-AR could alter scar pigmentation so as to improve skin scar colour match or reduce scar hyperpigmentation.

The inventor's findings that an agent which positively modulates β2-AR (such as a β2-AR agonist), improves skin scar colour matching, for example reduces scar hyperpigmentation, were unexpected for at least the following reason. Beta adrenoreceptor, for example β2-AR, activation has been linked with melanogenesis and tanning in response to UVB exposure. Beta adrenoreceptor, for example β2-AR, antagonists have been reported to be useful in bleaching the skin. Accordingly, it was surprising to find that in scar formation, β2-AR agonists instead were useful in improving skin scar colour matching, for example in reducing scar hyperpigmentation. Thus, instead of leading to darkening of the scar (as would be expected in view of the role of β2-AR activation in tanning and the effect of (β2-AR antagonists in lightening skin tone), β2-AR agonists instead reduce scar hyperpigmentation. See Example 2 below for further discussion of the role of the beta-adrenoreceptor in melanogenesis.

The subject may be a subject in need of improving skin scar colour matching, for example reducing scar hyperpigmentation, because the subject has or is at risk of hyperpigmentation. A subject (typically a human subject) may be selected as being at risk of hyperpigmentation on the basis of one or more of the following factors:

the subject has previously developed hyperpigmentation of a scar (which may be determined by questioning or examining the subject or subject's representative)

the subject tans readily on exposure to sunshine or ultraviolet (UV) radiation, rather than burning (which may be determined by questioning or examining the subject or subject's representative)

the subject has a non-Caucasian racial origin (which may be determined by questioning or examining the subject or subject's representative)

the subject's skin colour (for example in an area that is not tanned) is considered to be darker than that typical of a naturally fair-haired Caucasian person.

Thus, for example, the human subject may be selected as being at risk of hyperpigmentation because they are at least predominantly of Chinese, black African, Asian or Southern European racial origin, which may typically be determined by examination (for example based on general appearance) and/or questioning or genetic investigations/information. The subject may be selected as being at risk of hyperpigmentation based on their classification under the Fitzpatrick Scale (also known as the Fitzpatrick skin typing test or Fitzpatrick phototyping scale), which is a numerical classification schema for the colour of skin, as noted above. It was developed in 1975 by Thomas B. Fitzpatrick, a Harvard dermatologist, as a way to classify the response of different types of skin to UV light, and remains a recognized tool for dermatologic research into the color of skin. As noted above, the Fitzpatrick scale has the following skin types:

Type I (scores 0-7) Light, pale white.
Always burns, never tans
Type II (scores 8-16) White; fair.
Usually burns, tans with difficulty
Type III (scores 17-24) Medium, white to light brown.
Sometimes mild burn, gradually tans to a light brown
Type IV (scores 25-30) Olive, moderate brown.
Rarely burns, tans with ease to a moderate brown.
Type V (scores over 30) Brown, dark brown.
Very rarely burns, tans very easily
Type VI Black, very dark brown to black.
Never burns, tans very easily, deeply pigmented.

Thus, the subject (for example a human subject) may be selected as being at risk of hyperpigmentation if their skin type can be assessed as Type III or higher (i.e., Type, III, IV, V or VI) on the Fitzpatrick scale (whether or not it is formally expressed in terms of the Fitzpatrick scale).

A "subject" may be a human or, in experimental models, a porcine subject. Porcine skin is recognised as being a suitable animal model for human skin. Anatomically and physiologically, porcine skin is very similar to human skin (Montagna W, Yun J S (1964) The Skin of the Domestic Pig. The Journal of investigative dermatology 42: 11-21. Typically, the subject is a human being.

The skilled technician will appreciate what is meant by the terms "beta adrenergic receptor" and "β2-adrenergic receptor" or "β2-AR". These receptors are known in the art and have been reviewed in Johnson M, (*J Allergy Clin. Immunol.* (2006) 117, 18-24). However, for the avoidance of doubt, adrenergic receptors are a class of G protein-coupled receptors which bind and are activated by their endogenous ligands, the catecholamines, adrenaline and noradrenaline. The adrenergic receptors fall into 5 types: α1, α2, β1, β2, and β3, and the present invention is concerned with the beta adrenergic receptors, including the β2-adrenergic receptor (ie (β2-AR). The DNA and protein sequences for the human beta adrenergic receptors, for example β2-adrenergic receptor are available on freely accessible databases and are discussed in Kobilka et al (1987 *PNAS* 84, 46-50). The chromosomal location for the gene encoding the β2-adrenergic receptor is chromosome Sq 31-32. Additionally, the crystal structure for the β2-AR is available (Rasmussen S et al *Nature* (2007) 450, 383-387).

By the term "positively modulate β2-adrenergic receptor conformation", we mean the agent (or modulator) is capable of altering the three-dimensional shape and configuration of the receptor from its inactive to active conformation.

Preferably, the agent, which positively modulates β2-AR in accordance with the invention, is capable of selectively modulating the β2-adrenergic receptor conformation, or receptor activity, or activation thereof. Hence, the agent is a β2-AR-selective positive modulator.

By the term "selectively modulate", we mean that the agent alters β2-AR conformation, or enhances the β2-AR activity, or activation thereof to a greater extent, or at lower doses, than other types of adrenergic receptors, ie α1-, α2-, β1-, or β3-adrenergic receptors. Hence, it is preferred that the agent is selective for the beta adrenergic receptors, particularly for the β2-adrenergic receptor.

The chosen β2-AR-selective positive modulator may nevertheless be used at a concentration at which positive modulation of other beta adrenergic receptor or receptors also takes place. For example, at a concentration of salbutamol which is considered to be suitable for topical treatment (5 mM), it is expected that there would be activation of β1-ARs as well as β2-ARs. 5 mM salbutamol is reported to activate all βARs in Baker J G (2010) The selectivity of beta-adrenoceptor agonists at human beta1-, beta2- and beta3-adrenoceptors. British journal of pharmacology 160: 1048-1061.

The agent, which positively modulates β2-AR, may be capable of:—

(i) altering the conformational state of the receptor, for example by stabilizing the active conformation of the receptor and/or maintaining the receptor in its active conformation to thereby allow the receptor to bind its natural ligand, ie the catecholamines;

(ii) binding to the β2-adrenergic receptor, and increasing, promoting or augmenting transmission at the receptor;

(iii) promoting or activating the downstream signalling pathways activated by the modulator binding to the receptor;

(iv) increasing, promoting or augmenting transcription, translation or expression of the β2-adrenergic receptor;

(v) increasing synthesis or release of the β2-adrenergic receptor, or agonists thereof, from intracellular stores; or (vi) decreasing the rate of degradation of β2-adrenergic receptor, or agonists thereof.

It will be appreciated that each of mechanisms (i) to (vi) results in altering transmission at the receptor, and hence the activity thereof, to thereby positively modulate the β2-adrenergic receptor.

Suitably, the binding affinity value (Ki value) of the positive modulator for the β2-adrenergic receptor is less than about 100 nM, more suitably less than 80 nM, and more suitably less than 50 nM. Preferably, the Ki value of the positive modulator for the β2-adrenergic receptor is less than 30 nM, more preferably less than 15 nM, and more preferably less than 10 nM. As noted above, the positive modulator for the β2-adrenergic receptor may be used at concentrations considerably above these Ki values, for example in the mM range.

A preferred agent, which positively modulates β2-AR, is a β2-adrenergic receptor agonist.

By the term "agonist", we mean a molecule that selectively binds to the β2-adrenergic receptor to initiate the signal transduction reaction.

A suitable agonist may be selected from a list of agonists consisting of a simple chemical organic or inorganic compound; a peptide; a protein; a nucleic acid; a sugar; an antibody (or an active fragment thereof); or any other biological or chemical agent; each of which is capable of altering receptor conformation/stability, or inducing the receptor's activity.

The term β2-adrenergic receptor agonist, and many examples thereof, are well known to those skilled in the art.

As is also well known to those skilled in the art, examples of β2-adrenergic receptor agonists may include Levosalbutamol, Isoproterenol ($\beta_1$ and $\beta_2$), Metaproterenol, Terbutaline, Isoetarine, pirbuterol, procaterol, ritodrine, epinephrine, fenoterol, butoxamine, salbutamol, clenbuterol, formoterol, or salmeterol.

All of these, as well as other β2-adrenergic receptor agonists, are considered suitable for use in the present invention. However, a preferred β2-adrenergic receptor-selective agonist is salbutamol, as described in the Examples. Salbutamol is a highly selective β2-AR agonist, and will be known to the skilled technician.

The log $K_d$ (dissociation constant) of salbutamol for β1 is −4.66, for β3 is −4.33, and for β2 is −6.12. Hence, the log $K_d$ is much lower for β2-adrenergic receptor than for the β1- or the β3-AR. Salbutamol is therefore at least 29 times more selective for β2-AR than for the β1-AR, and 62 times more selective for β2-AR than for the β3-AR, and may therefore be described as being a β2-AR-selective agonist. As noted above, salbutamol (for example) may be used at concentrations at which it is able to bind to all beta adrenergic receptor subtypes. For Kd values, see, for example, Baker J G (2005) The selectivity of beta-adrenoceptor antagonists at the human beta1, beta2 and beta3 adrenoceptors. British journal of pharmacology 144: 317-322.

It will be appreciated that the ability of the medicaments and methods of the invention involving an agent which positively modulates β2-AR to improve scar skin colour match, for example to reduce hyperpigmentation, mean that these methods and medicaments are of value in a wide range of clinical settings. The methods and medicaments according to the invention may be used to improve scar skin colour match, for example to reduce hyperpigmentation, in the context of many different types of injury. For example, the methods and medicaments of the invention may be used improve scar skin colour match, for example to reduce hyperpigmentation, in scars arising from penetrating wounds or non-penetrating wounds formed as a result of physical insults or injuries including (but not limited to): grazes, abrasions, surgical incisions, and other surgical procedures (particularly partial thickness grafts of tissues such as the skin), "burns" (which, except for where the context requires otherwise, may be considered to include tissue damage resulting from exposure to either high or low temperature, chemical agents or radiation), post-inflammatory hyperpigmentation (for example following eczema, psoriasis or acne see, for example, http://www.patient.co.uk/doctor/Post-inflammatory-Hyperpigmentation-of-Skin.htm), and other forms of trauma, iatragenesis or genetic susceptibility.

By "trauma" we include the result of an incident of accidental or intentional acute injury to tissue (eg surgical incisions).

By "iatrogenic" we include the result of a medical treatment or therapy (eg radiotherapy; laser treatment).

It may be desirable to restrict application of the agent to the scar tissue itself (and tissue immediately adjacent to the scar) in order to minimise any potential darkening of the skin surrounding the scar. Typically the agent is applied into the initial wound to have the desired effect, as this may enhance reduction of hyperpigmentation by actively altering the cell behaviours during the wound healing process.

The agent may typically be applied topically but is also considered to be effective when used systemically. It is considered that there is no evidence that systemic salbutamol, for instance, via injected, oral or inhaled route, promotes skin pigmentation, even though o topical application of salbutamol to (non-damaged) skin is considered to promote skin pigmentation, as noted above. It is considered that systemic salbutamol in the blood is effective in the present invention, because it is delivered by capillaries into a wound site and is able to act to reduce hyperpigmentation of the wound, for example by reducing melanocyte recruitment to the wound.

It may be useful to useful to shield the wound from UV radiation. This may be achieved by a bandage or dressing (or similar), for example when the wound is open. When there is no open would and no bandage or dressing (or similar), for example when treating a scar undergoing remodelling, for example a just-healed scar, the application of a sunscreen, as well known to those skilled in the art, may be useful.

The present invention may be particularly useful in relation to more serious (for example typically larger and/or deeper) wounds, which may be more likely to develop hyperpigmentation. Typically scarring occurs when there has been damage to the dermis, but it is considered that hyperpigmentation may occur even without damage to the dermis (for example in a "scrape" injury).

The utility of the medicaments and methods of the invention are particularly suited to improve scar skin colour match, for example to reduce hyperpigmentation, in dermal wounds, ie wounds in the skin.

The present invention may also be useful in reducing hyperpigmentation in other wounds, for example corneal wounds or scars. See, for example, the following reference, which indicates that melanocytes are found in regions of the cornea: Rohrbach J M, Susskind D, Grub M (2012) [The melanocyte and the eye: a review with special emphasis on the cornea]. Klinische Monatsblatter fur Augenheilkunde 229: 42-47. The present invention may be useful in preventing or reducing melanocyte migration into a wound or scar of the cornea ie useful in reducing scar pigmentation (hyperpigmentation) in the cornea.

The medicaments and methods according to the invention may be used for improving the scar skin colour match, for example reducing hyperpigmentation, of a scar which may be selected from a group of scars consisting of acne scars, normal scars, scars from postinflammatory hyperpigmentation, keloid scars, hypertrophic scars and pterygium.

The methods and medicaments of the invention relating to agents which positively modulate β2-AR may be used in used for improving the scar skin colour match, for example reducing hyperpigmentation, which may be associated with grafting procedures. Treatment using the methods and medicaments of the invention will be beneficial both at a graft donor site (where it can aid reduction of hyperpigmentation and promote improved scar skin colour matching), and also at graft recipient sites (where it can also aid reduction of hyperpigmentation and promote improved scar skin colour matching). The inventor believes that the methods and medicaments of the invention confer advantages in the contexts of grafts utilising skin, artificial skin, or skin substitutes.

Medicaments according to the invention relating to agents which positively modulate β2-AR may be applied to a wound site or a site which may result in scarring, as a graft or patch beside, underneath, or on top of the affected area and adjacent healthy tissue, as is amply described in the published literature. Hence, it should be appreciated that the agent, which positively modulates β2-AR (eg an agonist), may be applied directly to the site to be treated. Alternatively, the positive modulator may be processed into a suitable therapeutically acceptable composition for subsequent application, such as an oil, cream, aerosol, hydrogel or liquid, depending on the treatment site, as described herein.

The medicaments relating to agents which positively modulate β2-AR may be used during skin transplantation, or as a biological dressing for burned skin, skin wounds, or as an adjunctive tissue in surgical reconstruction of artificial body parts.

The improvement of scar skin colour match, for example reduction in hyperpigmentation within the context of the present invention should be understood to encompass any improvement of scar skin colour match, for example reduction in hyperpigmentation as compared to the level of scar skin colour mismatch or hyperpigmentation occurring in a control-treated or untreated wound, ie one to which an agent, which positively modulates β2-AR, has not been administered. Typically they are used to improve scar skin colour match, for example reduce hyperpigmentation, in the skin of a patient who has been selected as being at risk of hyperpigmentation because their skin type can be assessed as Type III or higher (i.e., Type, III, IV, V or VI) on the Fitzpatrick scale. The reduction of hyperpigmentation or improvement in scar skin colour match achieved using methods and medicaments of the invention may be assessed with reference to either the microscopic and/or, preferably macroscopic, appearance of a treated scar as compared to the appearance of an untreated scar. More preferably, the reduction in hyperpigmentation or improvement in scar skin colour match may be assessed with reference to both macroscopic and microscopic appearance of a treated scar. By the term "treated scar", we mean a scar formed on healing of a treated wound, whereas an "untreated scar" means the scar formed on healing of an untreated wound, or a wound treated with a placebo or standard care. Suitable comparison scars may preferably be matched to the treated scar with reference to scar age, site, size and patient.

Methods for assessing scar skin colour match and scar hyperpigmentation will be known to those skilled in the art, as noted above. Any suitable method may be used, for example as set out above or in references [6]. [7], [8], [9]. For example, a scar assessment scale may be used, or a measurement device, which can give a measure of hyperpigmentation. Examples include a Mexameter or a DSM II Colourimeter, as mentioned above. A scar scale such as that described in Example 1 and FIG. 2 may be used, which assesses scar pigmentation (level of hyperpigmentation); colour match with surrounding tissue; and sheen.

It is considered that the methods, uses and medicaments of the invention will have other beneficial effects on the scar (for example as set out in WO 2009/118541 and as reported in Example 1). Parameters for the macroscopic assessment of scars may include: (i) height of the scar; (ii) area of the scar; and (iii) the stiffness of the scar. A treated scar may demonstrate a reduction in scarring as assessed with reference to at least one of the parameters for macroscopic assessment set out above. A treated scar may demonstrate reduced scarring with reference to at least two of the parameters or all three of these parameters (in addition to improved skin scar colour match, for example reduced hyperpigmentation).

Suitable parameters for the microscopic assessment of scars may include:—(i) thickness of extracellular matrix (ECM) fibres; (ii) orientation of ECM fibres; (iii) ECM composition of the scar; and (iv) the cellularity of the scar. A treated scar may demonstrate a reduction in scarring as assessed with reference to at least one of the parameters for microscopic assessment set out above. A treated scar may demonstrate reduced scarring with reference to at least two of the parameters, at least three of the parameters, or all four of these parameters (in addition to an improved macroscopic or microscopic assessment of scar skin colour match or hyperpigmentation). A microscopic assessment of scar skin colour match or hyperpigmentation may be based on number, size or colour or distribution of melanocytes within the scar area. A reduction or an improvement in scarring of a treated wound may further be assessed with reference to suitable parameters used in the:— i) macroscopic clinical assessment of scars, particularly the assessment of scars upon a subject;

ii) assessment of photographic images of scars; and iii) microscopic assessment of scars, for example by histological analysis of the microscopic structure of scars.

It will be appreciated that an improvement in scarring of a treated wound may be indicated by improvement of one or more such suitable parameters, and that in the case of an improvement as assessed with reference to a number of parameters, that these parameters may be combined from different assessment schemes (eg improvement in at least one parameter used in macroscopic assessment and at least one parameter used in microscopic assessment). A reduction or improvement in scarring may be demonstrated by an improvement in one or more parameters indicating that a treated scar more closely approximates unscarred skin with reference to the selected parameter(s) than does an untreated or control scar.

Suitable parameters for the clinical measurement and assessment of scars may be selected based upon a variety of measures or assessments including those described by Beausang et al (1998, *Plast. Reconstr. Surg.* 102 (6): 1954-1961) and van Zuijlen et al (2002, *Plast. Reconstr. Surg.* 109 (3): 1108-22). An overall assessment of scarring may be made using, for example, a Visual Analogue Scale or a digital assessment scale. Hence, typically, suitable parameters may include: assessment with regard to Visual Analogue Scale (VAS) scar score, scar height, scar width, scar perimeter, scar area or scar volume, appearance and/or colour of scar compared to surrounding unscarred skin, scar distortion and mechanical performance, scar contour and scar texture, collagen organisation, fibre thickness and fibre density. Each of these parameters will be known to the skilled technician. A reduction or improvement in scarring may be demonstrated by a change in any of these parameters such that a potential wound site or a scar treated with the positive modulator of β2-AR more closely resembles unscarred skin than does a control or untreated scar.

It is preferred that the subject or individual is one who does not suffer from a lupus erythromatosus, for example Discoid Lupus Erythematosus (DLE).

The inventor believes that the methods, uses and medicaments of the invention relating to agents which positively modulate β2-AR are able to improve scar skin colour match or reduce hyperpigmentation when administered either prior to wounding, or once a wound has already been formed. The methods or medicaments of the invention may be used prophylactically, ie at sites where no wound exists, but where a wound that would otherwise give rise to a scar or chronic wound may be formed. By way of example, medicaments in accordance with the invention may be administered to sites that are to undergo wounding as a result of elective procedures (such as surgery, eg plastic surgery), or to sites that are believed to be at elevated risk of wounding. It may be preferred that the medicaments of the invention are administered to the site immediately prior to the forming of a wound (for example in the period up to one hour, or up to six hours, before wounding).

The skilled technician will appreciate that the most preferred times of administration prior to formation of a wound will be determined with reference to a number of factors, including the formulation and route of administration of the selected medicament, the dosage of the medicament to be administered, the size and nature of the wound to be formed, and the biological status of the patient (which may be determined with reference to factors such as the patient's age, health, and predisposition to healing complications or adverse scarring). The prophylactic use of methods and medicaments in accordance with the invention is one preferred embodiment of the invention, and is particularly preferred in the improvement of scar skin colour matching or the reduction of hyperpigmentation in the context of surgical wounds.

The methods and medicaments of the invention are also useful to improve scar skin colour matching or the reduction of hyperpigmentation if administered after a wound has been formed. It is preferred that such administration should occur as early as possible after formation of the wound, but agents of the invention are able to improve scar skin colour matching or reduce hyperpigmentation at any time up until the healing process has been completed (ie even in the event that a wound has already partially healed, the methods and medicaments of the invention may be used to improve scar skin colour matching or reduce hyperpigmentation in respect of any remaining unhealed portion). It will be appreciated that the time-frame in which the methods and medicaments of the invention may be used to improve scar skin colour matching or reduce hyperpigmentation is dependent on the nature of the wound in question (including the degree of damage that has occurred, and the size of the wounded area). Thus, in the case of a large wound, the methods and medicaments of the invention may be administered relatively late in the healing response yet still be able to improve scar skin colour matching or reduce hyperpigmentation. The methods and medicaments of the invention may, for instance, preferably be administered within the first 24 hours after a wound is formed, but may still improve scar skin colour matching or reduce hyperpigmentation if administered up to two, three, four, five, six, seven, eight, nine or ten, or more, days after wounding.

The methods and medicaments of the invention may be administered on one or more occasions as may be necessary in order to improve scar skin colour matching or reduce hyperpigmentation. For instance, therapeutically effective amounts of the medicaments may be administered to a wound as often as required until the healing process has been completed to improve scar skin colour matching or reduce hyperpigmentation. Scars can remodel for as long as two years after healing. By way of example, the medicaments of the invention may be administered daily or twice daily to a wound for at least the first 14 days following the formation of the wound. The medicaments of the invention may be used for up to two months and possibly even longer for larger scars, for example for one or two years, whilst the scar is continuing to remodel. This may be determined by histological examination over time to see the changes in the collagen architecture in the wound bed.

Most preferably, the methods or medicaments of the invention may be administered after formation of a wound. It will be appreciated that the amount of a medicament of the invention that should be applied to a wound depends on a number of factors such as the biological activity and bioavailability of the agent present in the medicament, which in turn depends, among other factors, on the nature of the β2-adrenergic receptor agonist, and the mode of administration of the medicament.

Generally, when medicaments in accordance with the invention are used to treat existing wounds, the medicament should be administered as soon as the wound has occurred or been noticed (or in the case of wounds that are not immediately apparent, such as those at internal body sites, as soon as the wound has been diagnosed). Therapy with methods or medicaments in accordance with the invention should continue until the healing process has been completed, and scar skin colour match or hyperpigmentation improved, to a clinician's and patient's satisfaction.

It will be appreciated that the agent, which positively modulates β2-AR, and medicaments according to the invention may be used in a monotherapy (ie use of an agent, which positively modulates β2-AR conformation, or receptor activity or receptor activation alone), to improve scar skin colour matching or reduce hyperpigmentation. Alternatively, the agent, which positively modulates β2-AR, and medicaments according to the invention may be used as an adjunct to, or in combination with, known therapies for reducing scarring. For example, when the agent or medicament is used to improve scar skin colour matching or reduce hyperpigmentation, it may be used in combination with known anti-scarring therapeutics, such as corticosteroid injections, cryotherapy, topical silicone sheets, radiation, pressure garments and Imiquimod (Meier K and Nanney L, B, *Expert Opinion in Emerging Drugs* (2006) 11 (1), 39). It may be used in combination with a moisturiser, examples of which will be well known to those skilled in the art.

Medicaments of the invention may be administered by any suitable route capable of achieving the desired effect, of improving scar skin colour matching or reducing hyperpigmentation. It is preferred that the medicaments are administered locally at the wound site. Hence, the agent, which modulates β2-AR, and medicaments according to the invention may be combined in pharmaceutical compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a subject in need of treatment. It will be appreciated that the vehicle of medicaments according to the invention should be one which is well-tolerated by the subject to whom it is given. The vehicle or agent may be or may be incorporated into a plaster, bandage, wound dressing or other occlusive, protective product used in standard wound care.

Alternatively, or additionally, medicaments of the invention may be administered in a topical form. Such administration may be effected as part of the initial and/or follow up care for the wounded area. The inventors believe that improved scar skin colour matching or reduced hyperpigmentation is particularly improved by topical application of a β2-AR positive modulator to a wound (or, in the case of prophylactic application, to a tissue or site where a wound could be formed). Thus, for example, suitable medicaments may be in the form of a liquid, ointment, cream, gel, hydrogel, powder or aerosol. All of such compositions are suitable for topical application to a wound, which is a preferred means of administering the β2-AR positive modulator to a subject (eg a person or animal) in need of treatment. It is preferred that such formulations are applied directly to a wound site, (or at least adjacent a wound site). Thus, the formulation may be applied in and surrounding a wound site.

Alternatively, the β2-AR positive modulator or medicament may be provided on a vehicle (such as a sterile dressing or patch), which may be used to cover a wound site. Thus, the β2-AR positive modulator may for example be incorporated into a plaster, bandage, wound dressing or other occlusive, protective product used in standard wound and scar care. It will be appreciated that the vehicle should be one that is well-tolerated by the patient and allows release of the active agent to the wound. Such a vehicle is preferably biodegradeable, bioresolveable, bioresorbable and/or non-inflammatory.

The β2-AR positive modulator used in accordance with the invention may also be incorporated within a slow or delayed release device. Such devices may, for example, be inserted on or under the skin, and the medicament may be released over days, weeks or even months. The device may be located at least adjacent the treatment site, eg directly on a wound site. Preferably, the medicament is applied in and/or around a wound in order to improve scar skin colour matching or reduce hyperpigmentation. Such devices may be particularly advantageous when long-term treatment with the β2-AR positive modulator is required and which would normally require frequent administration (eg at least daily injection).

In one embodiment, a pharmaceutically vehicle for administration of the β2-AR positive or negative modulator may be a liquid, and a suitable pharmaceutical composition would be in the form of a solution. In another embodiment, the pharmaceutically acceptable vehicle is a solid, and a suitable composition of the medicament according to the invention is in the form of a powder or tablet. In a further embodiment, the β2-AR positive modulator may be formulated as a part of a pharmaceutically acceptable transdermal patch.

The inventors believe that optimum improvement in scar skin colour matching or reduction in hyperpigmentation may be effected by the administration of an agent, which positively modulates β2-AR, by injection at or around the wound site. For instance, in the case of dermal wounds, the positive modulator of β2-AR may be administered by means of intradermal injection. Thus, a preferred medicament in accordance with the invention comprises a solution of an agent, which positively modulates β2-AR, which is injectable directly into a site requiring treatment (eg for injection around the margins of a site of epithelial damage or a site likely to be damaged). Hence, in a preferred embodiment, the medicament may be injected into a wound, or the site of an impending surgical incision. Injections may be intravenous (bolus or infusion) or subcutaneous (bolus or infusion), or intradermal (bolus or infusion). It is also envisaged that medicaments according to the invention may be administered systemically to a subject by injection into the blood stream.

Although the utility of the medicaments and methods of the invention are particularly suited to reduce hyperpigmentation in dermal wounds, it will be appreciated that they may also be used to reduce hyperpigmentation of wounds in other tissues. Hyperpigmentation of scars produced by the healing of wounds in tissues other than the skin may also have detrimental effects. The scar may be internal or external, and may be on any part of the subject's body. Specific examples of such tissues include (but are not limited to) scars occurring as a result of wound healing in the central nervous system (eg following neuro-surgery or penetrating injuries of the brain); scars occurring as a result of wound healing in the eye; scarring occurring as a result of acne; scarring in the heart (eg following surgery or myocardial infarction); scars occurring as a result of wound healing involving the abdomen or pelvis; scarring arising as a result of wound healing in the pelvis in the region of the fallopian tubes; scarring following injury to muscles; and scarring or fibrosis following injury to tendons and ligaments.

Reduction of hyperpigmentation may be particularly important when treating ophthalmological conditions as a scar on the eye, which will often result in loss of vision quality. Hence, medicaments of the invention may be used in the treatment of ophthalmological conditions, such as persistent epithelial defects, neurotrophic keratitis, bullous keratopathy, excision of lesions, such as tumour of conjunctiva, and in association with stem cell transplant surgery.

Medicaments of the invention comprising the β2-AR positive modulator are suitable to be used for reducing hyperpigmentation in the cornea. Corneal wounds may result from trauma to the eye arising as a result of accidental injury, or as a result of surgical operations (eg laser surgery on the cornea). In this case, a preferred medicament of the invention may be in the form of an eye drop.

Medicaments comprising the agent, which positively modulates β2-AR, may be used to treat external wounds, ie on an external surface. However, medicaments comprising the β2-AR positive modulator may also be used to treat internal wounds, ie wounds occurring within the body on an internal surface. Thus, for example medicaments in accordance with the invention may be formulated for inhalation (eg an aerosol) for use in wounds arising in the lungs or other respiratory epithelia.

It will be appreciated that the amount of the β2-AR positive modulator that is required is determined by its biological activity and bioavailability, which in turn depends on the mode of administration, the physicochemical properties of the agent and whether the agent is being used as a monotherapy or in a combined therapy. The frequency of administration will also be influenced by the above-mentioned factors and particularly the half-life of the agent within the subject being treated. Optimal dosages to be administered may be determined by those skilled in the art, and will vary with the particular agent in use, the strength of the pharmaceutical composition, the mode of administration, and the advancement of the scarring disease. Additional factors depending on the particular subject being treated will result in a need to adjust dosages, including subject age, weight, gender, diet, and time of administration.

Typically the amount of a β2-AR modulator required for use in the individual to effect the treatment will be within the range of 0.001 ng to 100 mg of the agent per 24 hours, although this figure may be modified upwards or downwards in response to the factors outlined above. For treatment of a wound site, the amount of the β2-AR positive modulator to be administered may preferably be 50 to 500 ng per linear centimeter of epithelial damage in the wound site. Generally, a daily dose of between 0.001 µg/kg of body weight and 10 mg/kg of body weight of the β2-AR positive modulator may be used for improving skin colour matching or reducing hyperpigmentation depending upon which modulator is used. More preferably, the daily dose of the β2-AR positive modulator is between 0.1 mg/kg of body weight and 4 mg/kg of body weight, more preferably between 0.3 mg/kg and 2 mg/kg body weight, and most preferably between approximately 0.5 mg/kg and 1 mg/kg body weight. For example in the examples approximately 0.7 mg/kg/day was used in the pig study. The maximum human oral dose is considered to be around 0.65 mg/kg/day (as indicated on, for example the Ventolin (inhaled salbutamol) data sheet). See also, for example, Hutchings et at (1987) Br J Clin PHarmacol 24, 69-75 and Morgan et at (1986) Br J Clin Pharmacol 22, 587-593 which considered oral dosing. For example, 4 mg orally every 8 hours or iv at 400 µg/min both gave steady state plasma concentrations of around 10 ng/ml.

Frequency of administration will depend upon the biological half-life of the medicament used. Typically a cream or ointment containing the positive modulator of β2-AR should be administered to a target tissue such that the concentration of the modulator at the treatment site, such as a wound is maintained at a level suitable for having a therapeutic effect. This may require administration daily, or even several times daily. Daily doses o may be given as a single administration (eg a single daily injection or application of a volume of gel). Alternatively, the β2-AR positive modulator may require administration twice or more times during a day. As an example, the β2-AR positive modulator may be administered as two (or more, depending upon the severity of the condition being treated) daily doses of between 0.07 µg and 700 mg (ie assuming a body weight of 70 kg). A patient receiving treatment may take a first dose upon waking and then a second dose in the evening (if on a two dose regime), or doses at 3- or 4-hourly intervals.

Alternatively, a slow or delayed release device may be used to provide optimal doses of the β2-AR positive modulator to a patient without the need to administer repeated doses. Such devices may, for example, be placed on or inserted under the skin and the β2-AR positive modulator may be released over days, weeks or even months. Such a device may be particularly useful for patients that require long-term reduction of scarring or hyperpigmentation, for example in a remodelling scar (it may not be so useful for patients with a chronic wound. The devices may be particularly advantageous when used for the administration of a β2-AR positive modulator, which would normally require frequent administration (eg at least daily administration by other routes).

Known procedures, such as those conventionally employed by the pharmaceutical industry (eg in vivo experimentation, clinical trials, etc.), may be used to form specific formulations of the agents according to the invention and precise therapeutic regimes (such as daily doses of the agents and the frequency of administration).

Hence, in a further aspect of the invention, there is provided an anti-scar hyperpigmentation composition comprising a therapeutically effective amount of an agent, which positively modulates β2-AR conformation, or receptor activity, or activation thereof, and optionally a pharmaceutically acceptable vehicle; and optionally a UV absorbing agent (typically a dermally acceptable UV absorbing agent, such as used in a sunscreen composition). The composition may typically be for topical administration and may comprise a moisturiser and/or other components typically present in a sunscreen composition, for example. Sun screen compositions are described in, for example, WO2012170695, EP2529724, EP1928401.

By the term "anti-scar hyperpigmentation composition", we mean a pharmaceutical compound used in the therapeutic prevention, reduction or inhibition of scar hyperpigmentation in a patient.

The composition may be a cosmetic composition. It is preferred that the composition is a therapeutic composition.

The invention also provides in a further aspect, a process for making the composition according to the above aspects, the process comprising combining a therapeutically effective amount of an agent, which positively or negatively modulates β2-AR conformation, or receptor activity, or activation thereof (as the case may be), with a pharmaceutically acceptable vehicle and optionally other agents such as a UV absorbing agent.

The agent, which positively modulates β2-AR, in the composition according to the above aspects is preferably selective for β2-AR, and may be a β2-AR agonist. The agonist may be selected from a list of agonists consisting of a simple chemical organic or inorganic compound; a peptide; a protein; a nucleic acid; a sugar; an antibody (or an active fragment thereof); each of which are capable of altering receptor conformation/stability, or inducing the receptor's activity. The β2-AR-selective agonist may be Levosalbutamol, Isoproterenol ($\beta_1$ and $\beta_2$), Metaproterenol, Terbutaline, Isoetarine, pirbuterol, procaterol, ritodrine, epinephrine, fenoterol, butoxamine, salbutamol, clenbuterol, formoterol, or salmeterol, for example. However, a preferred β2-AR-selective agonist in the composition is salbutamol.

A "therapeutically effective amount" of agent is any amount which, when administered to a subject, results in an improvement in skin scar colour matching or a reduction in scar hyperpigmentation in the subject.

For example, the therapeutically effective amount of agent used may be from about 0.07 µg to about 700 mg, and preferably from about 0.7 µg to about 70 mg. It is preferred that the amount of agent is an amount from about 7 µg to about 15 mg for topical application, and from about 7 µg to about 700 µg for intravenous application.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

In a preferred embodiment, the pharmaceutical vehicle is a liquid or cream, and the pharmaceutical composition is in the form of a solution or a gel. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, eg cellulose derivatives, preferably sodium carboxymethyl cellulose solution), alcohols (including monohydric alcohols and polyhydric alcohols, eg glycols) and their derivatives, and oils (eg fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions which are sterile solutions or suspensions can be utilized by, for example, intramuscular, intrathecal, epidural, intraperitoneal, intravenous and particularly subcutaneous injection. The β2-AR positive modulator may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

A topical formulation may be particularly useful. A gel of hydrocolloid or other suitable composition, for example, may be useful, as it may stay in the wound for a useful period of time and provide release of the active agent or agents over time. See, for example, EP0928206, EP0567311. As noted above, a dressing formulation may also be particularly useful.

For a better understanding of the invention, and to show how embodiments of the same may be carried into effect, reference will now be made, by way of example, to the following Examples and accompanying Figures.

FIGURES

FIG. 1: Wound positions, showing position T/10

Figure 2:
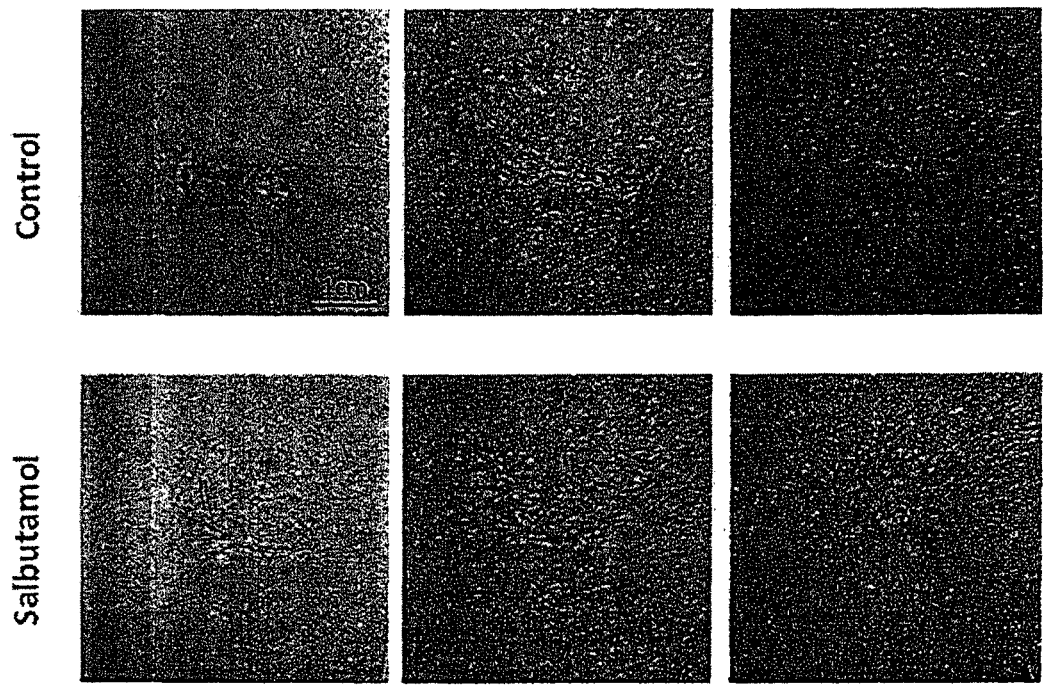

FIG. 2: Scar appearance at day 56—position T/10. Scaled and cropped pictures H8 cm ×W 7.11.

Figure 3:
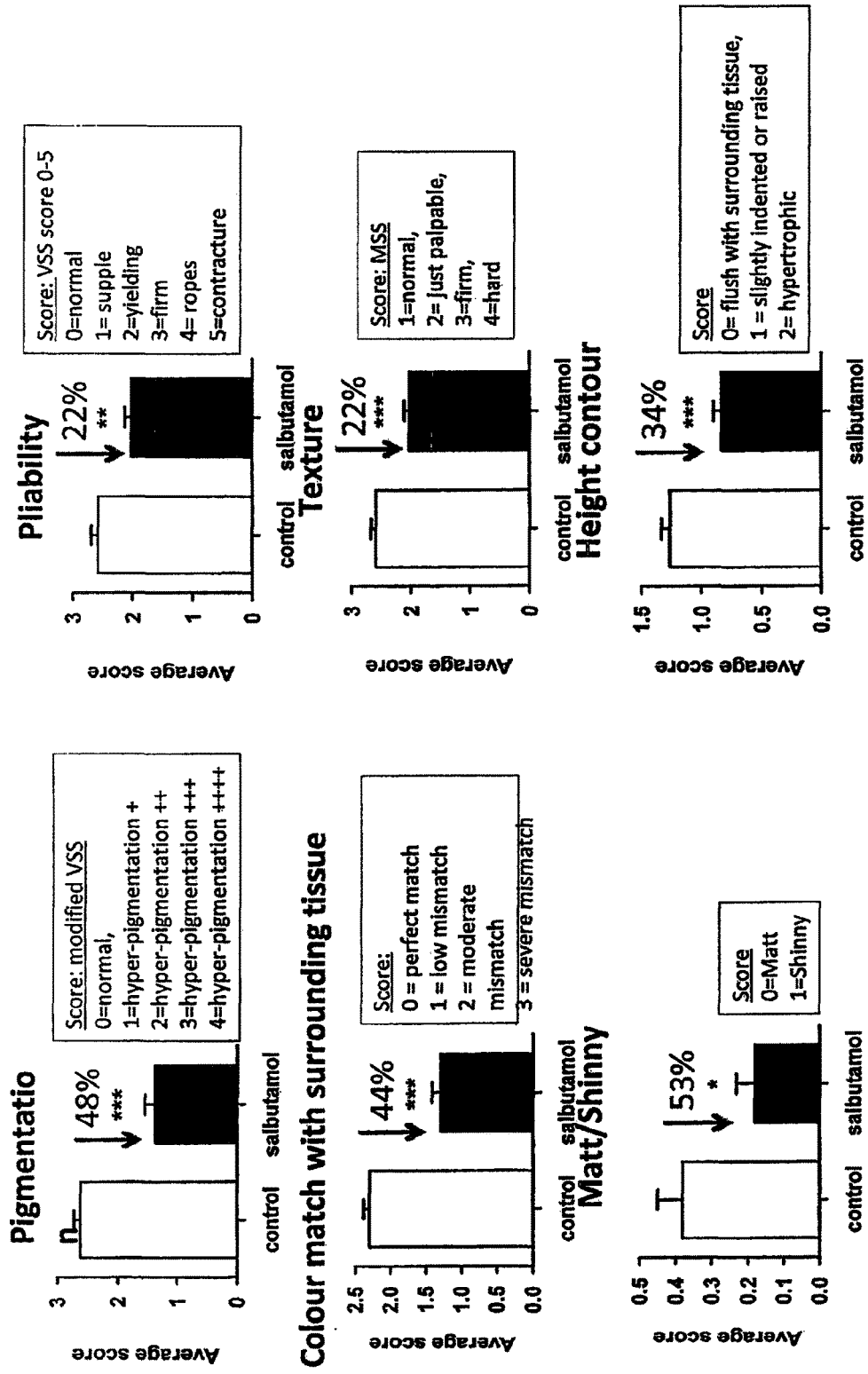

FIG. 3: Day 56—Scars. Salbutamol-treated scars were less hyper-pigmented, the scar colour matched better with surrounding tissue, they were more pliable and less firm, raised and shiny than control scars at day 56 post-wounding ($P<0.0001$).

Figure 4:
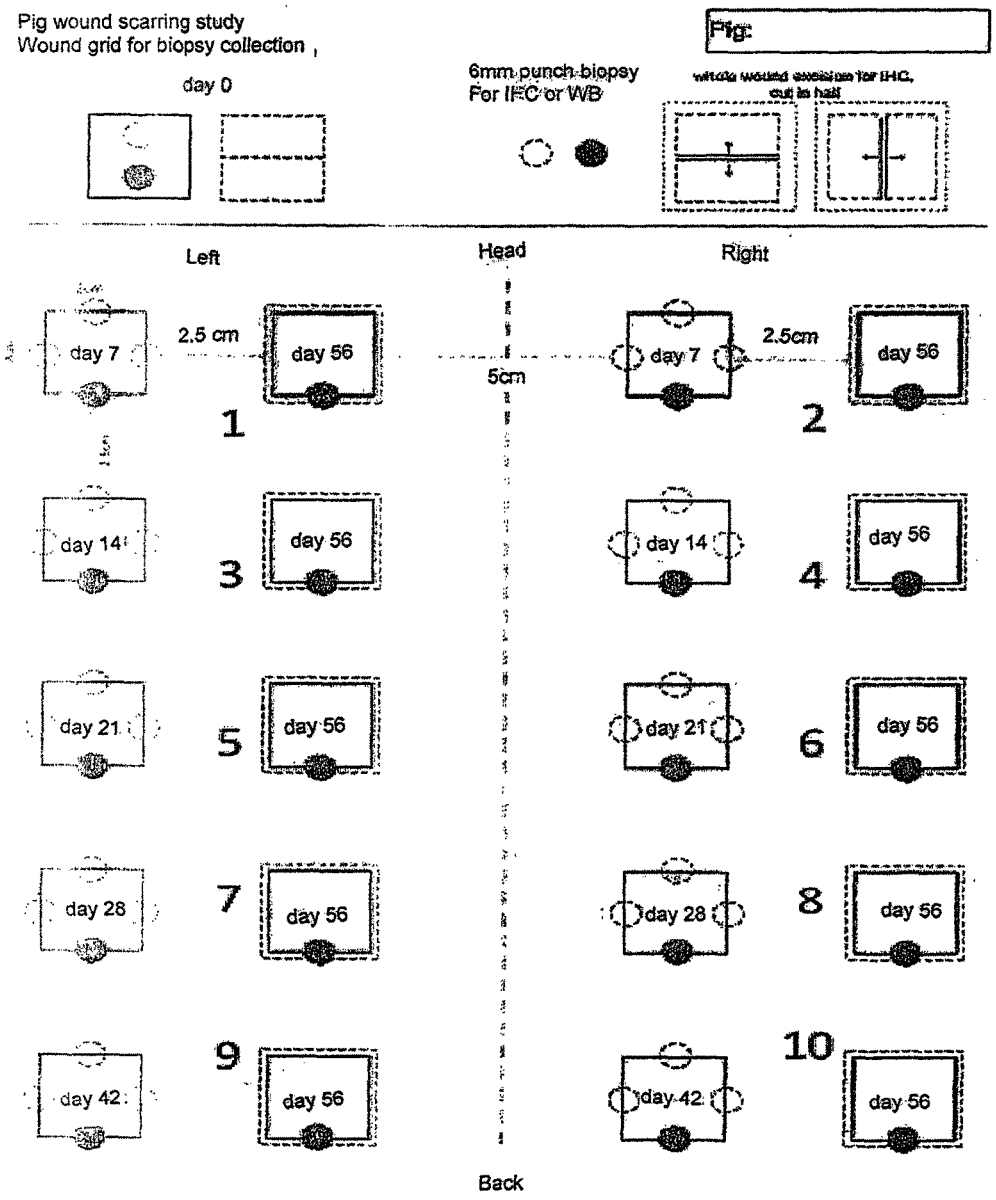

FIG. 4: Wound positions and biopsy sampling schedule

Figure 5:
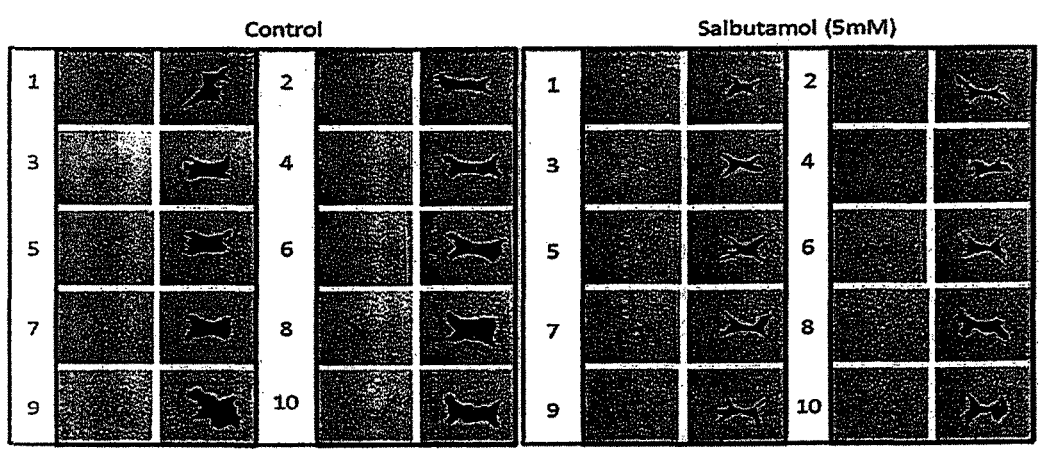

FIG. 5: Scar appearance

FIG. 6: Scar area

Figure 7:
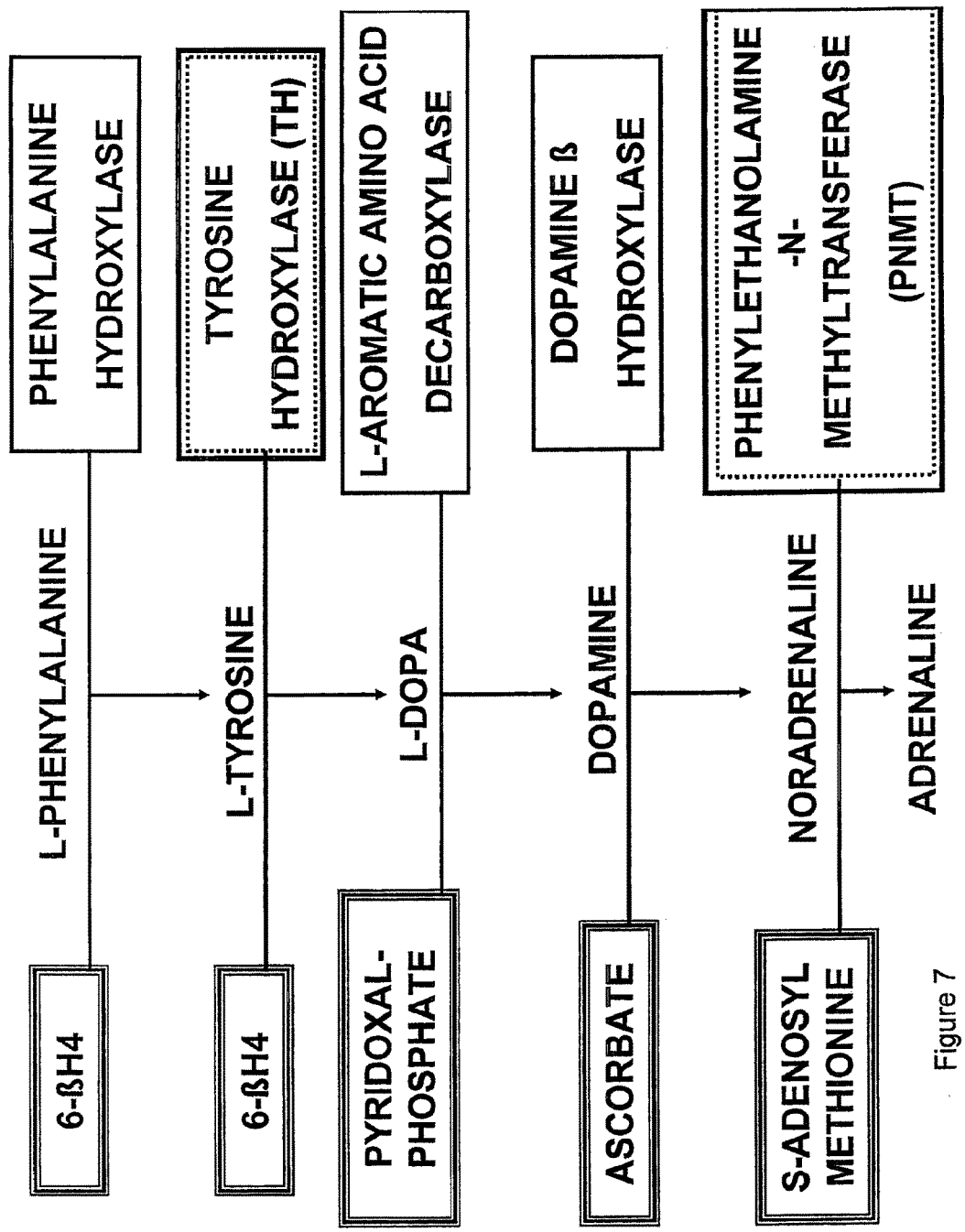

FIG. 7: melanogenesis

EXAMPLE 1

Salbutamol Reduces Scar Hyperpigmentation and Improves Skin-scar Colour Match in a Porcine Wound Model Red Duroc Model Anatomically and physiologically, porcine skin is very similar to human skin [19]. Wounds in small mammal skin, which is untethered, heal primarily by wound contraction [20], whereas porcine and human skin wounds close primarily by wound re-epithelialisation [21]. The Red Duroc pig is well established as a reproducible model of fibro proliferative and hypertrophic scar formation [22, 23]. Similar to human hypertrophic scars, Red Duroc pigs heal wounds with an excessive amount of collagen deposition and increased wound contraction [23]. In addition, the wounds heal with hyperpigmentation at the wound margins [22] creating hyperpigmented scars [24] and the scars are raised, similar to human scars [25]. Indeed, the Red Duroc scar model has been evaluated and used by multiple groups [26, 27, 28, 29] and is ideal for testing therapeutic interventions to reduce scarring [22, 26].

A porcine wound scar study was conducted in the Red Duroc pig. 4 rows of 5 (2×2 cm) full-thickness wounds were created, either side of the spine, on the shaved backs of 10 Red Durocs (FIGS. 1, 4). 5 control and 5 treatment pigs were treated with 500 µl of Granugel alone, or containing 5 mM salbutamol, per wound daily. Two wounds per animal were biopsied (6 mm punch) at 7, 14, 21, 28 and 42 days post wounding. The remaining 10 wound scars per animal were photographed and harvested at day 56 post-wounding, giving a total of 5 wounds per position, 50 wounds in total for each group.

A number of scales have been developed to score the severity of human scars. The Vancouver scar scale (VSS) [7], the Manchester scar scale (MSS) [8] and the patient and observer scar assessment scale (POSAS) [9]. We developed our own scale to score the severity of the Red Duroc scars based on the VSS [7] and the MSS [8]. The patient and observer scar assessment scale (POSAS) could not be used as it requires patient involvement [9].

The VSS measures four parameters: pigmentation, vascularity, pliability and height [7], while the MSS measures colour, contour, distortion and texture [8]. Our scar scale was developed to score a number of scar characteristics including: pigmentation, colour match with surrounding tissue, skin sheen, pliability, texture and height contour.

Salbutamol treatment significantly improved the scores for pigmentation, colour match and sheen by 48%, 44% and 53%, respectively (FIG. 2). Pliability, texture and height contour scores improved by 22%, 22% and 34%, respectively.

The best three scars at position 10 (FIG. 1) from control and salbutamol-treated wounds are shown (FIG. 3).

In conclusion, salbutamol treatment significantly improved scar hyperpigmentation in a well-known scar/wound hyperpigmentation model.

Other Parameters

Figure 6A:
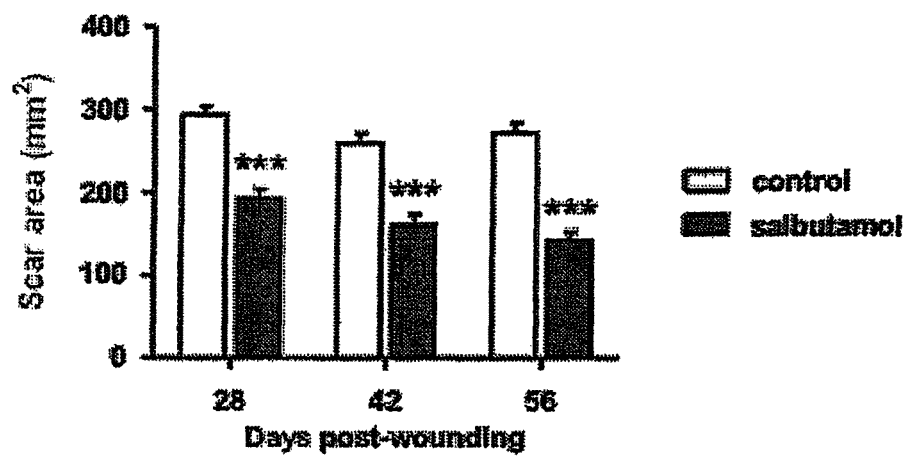

The scar closest to the average scar area, at each position, for both control and sal-treated wounds are presented (FIG. 5b). Scar area was reduced by 47.1% upon sal treatment, 56 days post wounding (FIG. 6a). Indeed, by day 28 and 42 post-wounding the scar area of the sal-treated wounds was already 34.1% and 37.7% smaller than control wounds (FIG. 6a; ***$P<0.001$).

Figure 6B:
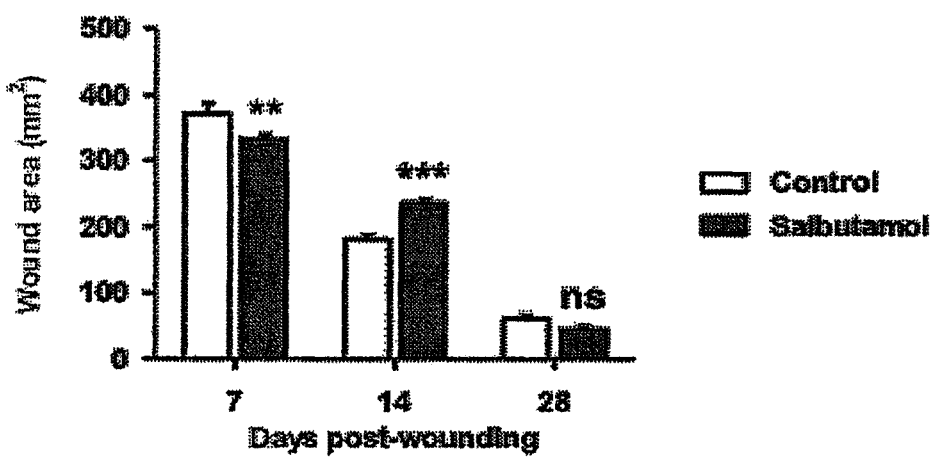

Wound area was also measured in early time points. No significant difference was observed in re-epithelialisation rates between control and sal-treated wounds (results not shown). Sal-treated wounds were significantly less swollen (11% smaller) after 7 days, indicating a reduction in wound inflammation, which will be confirmed by immunohistochemistry (IHC). After 14 days, Sal-treated wounds were significantly less contracted (23% larger) than control wounds, indicating a reduction in fibroblast function, and by 28 days the sal-treated wounds were slightly smaller than control wounds (FIG. 6b; $P<0.01$; *$P<0.001$).

REFERENCES

1. Fitzpatrick T B (1988) The validity and practicality of sun-reactive skin types I through VI. Archives of dermatology 124: 869-871.
2. Lear J T, Tan B B, Smith A G, Bowers W, Jones P W, et al. (1997) Risk factors for basal cell carcinoma in the UK: case-control study in 806 patients. Journal of the Royal Society of Medicine 90: 371-374.
3. Elwood J M, Gallagher R P, Hill G B, Spinelli J J, Pearson J C, et al. (1984) Pigmentation and skin reaction to sun as risk factors for cutaneous melanoma: Western Canada Melanoma Study. British medical journal 288: 99-102.
4. Pathac Ma F T (1993) Preventative treatment of sun burn, dermatoheliosis, and skin cancer with sun protective agents. In: Fitzpatrick T, Eisen A Z, Wolff K, editor. Dermatology in general medicine. 4th edition ed. New York: McGraw-Hill Inc. pp. 1689-1717.
5. Nieuweboer-Krobotova L (2013) Hyperpigmentation: types, diagnostics and targeted treatment options. Journal of the European Academy of Dermatology and Venereology: JEADV 27 Suppl 1: 2-4.
6. van der Wal M, Bloemen M, Verhaegen P, Tuinebreijer W, de Vet H, et al. (2012) Objective Color Measurements: Clinimetric Performance of Three Devices on Normal Skin and Scar Tissue. Journal of burn care & research: official publication of the American Burn Association.
7. Sullivan T, Smith J, Kermode J, McIver E, Courtemanche D J (1990) Rating the burn scar. The Journal of burn care & rehabilitation 11: 256-260.
8. Beausang E, Floyd H, Dunn K W, Orton C I, Ferguson M W (1998) A new quantitative scale for clinical scar assessment. Plastic and reconstructive surgery 102: 1954-1961.
9. Draaijers L J, Tempelman F R, Botman Y A, Tuinebreijer W E, Middelkoop E, et al. (2004) The patient and observer scar assessment scale: a reliable and feasible tool for scar evaluation. Plastic and reconstructive surgery 113: 1960-1965; discussion 1966-1967.
10. Halder R M, Brooks H L, Callender V D (2003) Acne in ethnic skin. Dermatologic clinics 21: 609-615, vii.
11. Halder R M, Nandedkar M A, Neal K W (2003) Pigmentary disorders in ethnic skin. Dermatologic clinics 21: 617-628, vii.
12. Halder R M, Nootheti P K (2003) Ethnic skin disorders overview. Journal of the American Academy of Dermatology 48: S143-148.
13. Coley M K, Alexis A F (2009) Managing common dermatoses in skin of color. Seminars in cutaneous medicine and surgery 28: 63-70.
14. King R, Googe P B, Page R N, Mihm M C, Jr. (2005) Melanocytic lesions associated with dermatofibromas: a spectrum of lesions ranging from junctional nevus to malignant melanoma in situ. Modern pathology: an official journal of the United States and Canadian Academy of Pathology, Inc 18: 1043-1047.
15. Konda S, Geria A N, Halder R M (2012) New horizons in treating disorders of hyperpigmentation in skin of color. Seminars in cutaneous medicine and surgery 31: 133-139.
16. Sina B, Goldner R (1990) Malignant melanoma and pigmented lesions: a diagnostic and management dilemma. Southern medical journal 83: 1218-1223.
17. Levesque M, Feng Y, Jones R A, Martin P (2013) Inflammation drives wound hyperpigmentation in zebrafish by recruiting pigment cells to sites of tissue damage. Disease models & mechanisms.
18. Galko M J, Krasnow M A (2004) Cellular and genetic analysis of wound healing in Drosophila larvae. PLoS biology 2: E239.
19. Montagna W, Yun J S (1964) The Skin of the Domestic Pig. The Journal of investigative dermatology 42: 11-21.
20. Hayward P G, Robson M C (1991) Animal models of wound contraction. Progress in clinical and biological research 365: 301-312.
21. Sullivan T P, Eaglstein W H, Davis S C, Mertz P (2001) The pig as a model for human wound healing. Wound Repair Regen 9: 66-76.
22. Gallant C L, Olson M E, Hart D A (2004) Molecular, histologic, and gross phenotype of skin wound healing in red Duroc pigs reveals an abnormal healing phenotype of hypercontracted, hyperpigmented scarring. Wound repair and regeneration: official publication of the Wound Healing Society [and] the European Tissue Repair Society 12: 305-319.
23. Gallant-Behm C L, Hart D A (2006) Genetic analysis of skin wound healing and scarring in a porcine model. Wound repair and regeneration: official publication of the Wound Healing Society [and] the European Tissue Repair Society 14: 46-54.
24. Gallant-Behm C L, Reno C, Tsao H, Hart D A (2007) Genetic involvement in skin wound healing and scarring in domestic pigs: assessment of molecular expression patterns in (Yorkshire×Red Duroc)×Yorkshire backcross animals. The Journal of investigative dermatology 127: 233-244.
25. Zhu K Q, Carrougher G J, Gibran N S, Isik F F, Engrav L H (2007) Review of the female Duroc/Yorkshire pig model of human fibroproliferative scarring. Wound Repair Regen 15 Suppl 1: S32-39.
26. Gallant-Behm C L, Hildebrand K A, Hart D A (2008) The mast cell stabilizer ketotifen prevents development of excessive skin wound contraction and fibrosis in red Duroc pigs. Wound Repair Regen 16: 226-233.
27. Harunari N, Zhu K Q, Armendariz R T, Deubner H, Muangman P, et al. (2006) Histology of the thick scar on the female, red Duroc pig: final similarities to human hypertrophic scar. Burns 32: 669-677.
28. Gurtner G C, Dauskardt R H, Wong V W, Bhatt K A, Wu K, et al. (2011) Improving cutaneous scar formation by controlling the mechanical environment: large animal and phase I studies. Annals of surgery 254: 217-225.
29. Liang Z, Xie C Y, Lin H B, Guo Z D, Yang W G (2006) [Pathomorphological observation of the hypertrophic scar induced by injury to conical structure in female red Duroc pig]. Zhonghua shao shang za zhi=Zhonghua shaoshang zazhi=Chinese journal of burns 22: 29-32.

EXAMPLE 2

Role of the Beta-adrenoceptor in Melanogenesis

The catecholamines noradrenaline and adrenaline, are synthesized by a series of enzymes (FIG. 7) in the central nervous system, sympathetic nerves and the chromaffin cells of the adrenal medulla and act as neurotransmitters and endocrine hormones [1]. In addition, a number of reports have demonstrated that the cells of the epidermis, keratinocytes, express the key enzymes that convert L-tyrosine to noradrenaline (tyrosine hydroxylase (TH)) and adrenaline (phenylethanolamine-N-methyltransferase (PNMT)) [2, 3] and, indeed, can secrete adrenaline [4]. In contrast, melanocytes express the enzymes to synthesise noradrenaline, including tyrosine hydroxylase, but not adrenaline [5].

The catecholamines act through adrenergic receptors [6], classified into alpha and beta adrenoceptors on the basis of their pharmacology [7] The Beta-adrenergic receptors (βARs; β1AR, β2AR, β3AR) are G protein-coupled receptors recognized as pivotal functional regulators of the cardiac, pulmonary, vascular, endocrine and central nervous systems [8].

Recent work has revealed that the β2AR is also an important functional regulator in skin. The β2AR is highly expressed on all cell lineages in skin [9, 10, 11, 12, 13] (reviewed in [14]) including keratinocytes [13, 15] and melanocytes [5], therefore, a functional autocrine and paracrine beta adrenergic network exists in the epidermis and the dermis, respectively. The beta adrenergic network plays a role in keratinocyte differentiation [16] vitiligo [2, 17], atopic eczema [2] and wound repair [4, 14, 18, 19, 20, 21, 22, 23, 24, 25, 26, 27, 28, 29, 30, 31, 32, 33]

In particular, recent research has revealed a role for the beta adrenergic network in skin pigmentation. Adrenaline secreted from keratinocytes specifically increased melanin production in melanocytes via the β2AR and the downstream elevation of cAMP [5]. In addition, the catecholamine synthesis enzyme TH acts in concert with tyrosinase in the melanocyte to promote pigmentation [34]. Indeed, it is well known that exposure to UV radiation induces skin hyperpigmentation or tanning. Under experimental conditions, UVB exposure induced adrenaline release from keratinocytes, which activated melanogenesis in melanocytes [35], via β2AR activation [5], while noradrenaline had no effect [35], supporting a paracrine beta adrenergic mechanism for UV-induced melanogenesis in the skin. Moreover, expression profiling of the UVB response in melanocytes has identified the β2AR gene (ADRB2) as a gene that was up-regulated 2.8 fold upon UV radiation exposure. In addition, ADRB2 expression was also lost in melanomas, suggesting a possible protective role in melanoma [36]. Finally, several orthologs of beta adrenoceptors have been discovered in zebrafish, which differed in their expression patterns. Adrb2a, the ortholog of β2AR, was expressed in brain and skin and the knock-down of adrb2a revealed a function role in pigmentation [37]. Indeed, gene expression profiling of age spots (solar lentigo) revealed that δAR expression was elevated in the age spot compared to noninvolved skin [38]. In melanoma cells, siRNA knock-down of either β1AR or β2AR reduced melanin production to only 31% and 39% of control production, respectively, while βAR agonists increased melanin synthesis by 150% [38]. In contrast, a βAR antagonist, undecylenoyl phenylalanine, suppressed melanin production and had a skin lightening effect {Gillbro, 2011 #5810}, when added topically to Chinese females with age spots [38].

In summary, evidence supports the hypothesis that β2AR activation promotes melanogenesis, increasing skin pigmentation.

REFERENCES

1. Schulz C, Eisenhofer G, Lehnert H (2004) Principles of catecholamine biosynthesis, metabolism and release. Front Horm Res 31: 1-25.
2. Schallreuter K U (1997) Epidermal adrenergic signal transduction as part of the neuronal network in the human epidermis. J Investig Dermatol Symp Proc 2: 37-40.
3. Schallreuter K U, Wood J M, Lemke R, LePoole C, Das P, et al. (1992) Production of catecholamines in the human epidermis. Biochem Biophys Res Commun 189: 72-78.
4. Pullar C E, Rizzo A, Isseroff R R (2006) beta-Adrenergic receptor antagonists accelerate skin wound healing: evidence for a catecholamine synthesis network in the epidermis. J Biol Chem 281: 21225-21235.
5. Gillbro J M, Manes L K, Hibberts N A, Schallreuter K U (2004) Autocrine catecholamine biosynthesis and the beta-adrenoceptor signal promote pigmentation in human epidermal melanocytes. J Invest Dermatol 123: 346-353.
6. Cotecchia S, Stanasila L, Diviani D (2012) Protein-protein interactions at the adrenergic receptors. Current drug targets 13: 15-27.
7. Ahlquist R P (1948) A study of the adrenotropic receptors. The American journal of physiology 153: 586-600.
8. Wallukat G (2002) The beta-adrenergic receptors. Herz 27: 683-690.
9. de Coupade C, Gear R W, Dazin P F, Sroussi H Y, Green P G, et al. (2004) Beta 2-adrenergic receptor regulation of human neutrophil function is sexually dimorphic. Br J Pharmacol 143: 1033-1041.
10. Iaccarino G, Cipolletta E, Fiorillo A, Annecchiarico M, Ciccarelli M, et al. (2002) Beta(2)-adrenergic receptor gene delivery to the endothelium corrects impaired adrenergic vasorelaxation in hypertension. Circulation 106: 349-355.
11. Izeboud C A, Mocking J A, Monshouwer M, van Miert A S, Witkamp R F (1999) Participation of beta-adrenergic receptors on macrophages in modulation of LPS-induced cytokine release. J Recept Signal Transduct Res 19: 191-202.
12. McSwigan J D, Hanson D R, Lubiniecki A, Heston L L, Sheppard J R (1981) Down syndrome fibroblasts are hyperresponsive to beta-adrenergic stimulation. Proc Natl Acad Sci USA 78: 7670-7673.
13. Steinkraus V, Steinfath M, Korner C, Mensing H (1992) Binding of beta-adrenergic receptors in human skin. J Invest Dermatol 98: 475-480.
14. Pullar C E, Manabat-Hidalgo C G, Bolaji R S, Isseroff R R (2008) beta-Adrenergic receptor modulation of wound repair. Pharmacol Res 58: 158-164.
15. Steinkraus V, Korner C, Steinfath M, Mensing H (1991) High density of beta 2-adrenoceptors in a human keratinocyte cell line with complete epidermal differentiation capacity (HaCaT). Arch Dermatol Res 283: 328-332.
16. Schallreuter K U, Lemke K R, Pittelkow M R, Wood J M, Korner C, et al. (1995) Catecholamines in human keratinocyte differentiation. J Invest Dermatol 104: 953-957.
17. Schallreuter K U, Wood J M, Pittelkow M R, Swanson N N, Steinkraus V (1993) Increased in vitro expression of beta 2-adrenoceptors in differentiating lesional keratinocytes of vitiligo patients. Arch Dermatol Res 285: 216-220.
18. Pullar C E, Chen J, Isseroff R R (2003) PP2A activation by beta2-adrenergic receptor agonists: novel regulatory mechanism of keratinocyte migration. J Biol Chem 278: 22555-22562.
19. Pullar C E, Grahn J C, Liu W, Isseroff R R (2006) Beta2-adrenergic receptor activation delays wound healing. Faseb J 20: 76-86.
20. Pullar C E, Isseroff R R (2005) Cyclic AMP mediates keratinocyte directional migration in an electric field. J Cell Sci 118: 2023-2034.
21. Pullar C E, Isseroff R R (2005) Beta 2-adrenergic receptor activation delays dermal fibroblast-mediated contraction of collagen gels via a cAMP-dependent mechanism. Wound Repair Regen 13: 405-411.

22. Pullar C E, Isseroff R R (2006) The beta 2-adrenergic receptor activates pro-migratory and pro-proliferative pathways in dermal fibroblasts via divergent mechanisms. J Cell Sci 119: 592-602.
23. Pullar C E, Isseroff R R, Nuccitelli R (2001) Cyclic AMP-dependent protein kinase A plays a role in the directed migration of human keratinocytes in a DC electric field. Cell Motil Cytoskeleton 50: 207-217.
24. Pullar C E, Le Provost G S, O'Leary A P, Evans S E, Baier B S, et al. (2012) beta2AR Antagonists and beta2AR Gene Deletion Both Promote Skin Wound Repair Processes. The Journal of investigative dermatology β2: 2076-2084.
25. Romana-Souza B, Monte-Alto-Costa A (2009) Simultaneous blockade of alpha and beta adrenoceptors impairs cutaneous wound healing in rats. J Eur Acad Dermatol Venereol.
26. Romana-Souza B, Monte-Alto-Costa A (2010) Simultaneous blockade of alpha and beta adrenoceptors impairs cutaneous wound healing in rats. Journal of the European Academy of Dermatology and Venereology: JEADV 24: 349-352.
27. Romana-Souza B, Nascimento A P, Monte-Alto-Costa A (2008) Low-dose propranolol improves cutaneous wound healing of burn-injured rats. Plast Reconstr Surg 122: 1690-1699.
28. Romana-Souza B, Nascimento A P, Monte-Alto-Costa A (2009) Propranolol improves cutaneous wound healing in streptozotocin-induced diabetic rats. Eur J Pharmacol 611: 77-84.
29. Romana-Souza B, Otranto M, Vieira A M, Filgueiras C C, Fierro I M, et al. (2010) Rotational stress-induced increase in epinephrine levels delays cutaneous wound healing in mice. Brain, behavior, and immunity 24: 427-437.
30. Romana-Souza B, Porto L C, Monte-Alto-Costa A (2010) Cutaneous wound healing of chronically stressed mice is improved through catecholamines blockade. Experimental dermatology 19: 821-829.
31. Romana-Souza B, Santos J S, Costa A M (2006) Blockade of β1- and β2-Adrenoceptors delays wound contraction and re-epithelialization in rats. Clinical and experimental pharmacology and physiology 33: p 421-430.
32. Romana-Souza B, Santos J S, Monte-Alto-Costa A (2009) beta-1 and beta-2, but not alpha-1 and alpha-2, adrenoceptor blockade delays rat cutaneous wound healing. Wound Repair Regen 17: 230-239.
33. Sivamani R K, Pullar C E, Manabat-Hidalgo C G, Rocke D M, Carlsen R C, et al. (2009) Stress-Mediated Increases in Systemic and Local Epinephrine Impair Skin Wound Healing: Potential New Indication for Beta Blockers. PLoS Med 6: e12.
34. Marles L K, Peters E M, Tobin D J, Hibberts N A, Schallreuter K U (2003) Tyrosine hydroxylase isoenzyme I is present in human melanosomes: a possible novel function in pigmentation. Experimental dermatology 12: 61-70.
35. Sivamani R K, Porter S M, Isseroff R R (2009) An epinephrine-dependent mechanism for the control of UV-induced pigmentation. The Journal of investigative dermatology 129: 784-787.
36. Yang G, Zhang G, Pittelkow M R, Ramoni M, Tsao H (2006) Expression profiling of UVB response in melanocytes identifies a set of p53-target genes. The Journal of investigative dermatology 126: 2490-2506.
37. Wang Z, Nishimura Y, Shimada Y, Umemoto N, Hirano M, et al. (2009) Zebrafish beta-adrenergic receptor mRNA expression and control of pigmentation. Gene 446: 18-27.
38. Osborne R, Hakozaki T, Laughlin T, Finlay D R (2012) Application of genomics to breakthroughs in the cosmetic treatment of skin ageing and discoloration. The British journal of dermatology 166 Suppl 2: 16-19.
39. Whelan C J, Johnson M, Vardey C J (1993) Comparison of the anti-inflammatory properties of formoterol, salbutamol and salmeterol in guinea-pig skin and lung. British journal of pharmacology 110: 613-618.
40. Renshaw S A, Loynes C A, Elworthy S, Ingham P W, Whyte M K (2007) Modeling inflammation in the zebrafish: how a fish can help us understand lung disease. Exp Lung Res 33: 549-554.
41. Renshaw S A, Loynes C A, Trushell D M, Elworthy S, Ingham P W, et al. (2006) A transgenic zebrafish model of neutrophilic inflammation. Blood 108: 3976-3978.
42. Levesque M, Feng Y, Jones R A, Martin P (2013) Inflammation drives wound hyperpigmentation in zebrafish by recruiting pigment cells to sites of tissue damage. Disease models & mechanisms.
43. Galko M J, Krasnow M A (2004) Cellular and genetic analysis of wound healing in Drosophila larvae. PLoS biology 2: E239.
44. Sugata K, Kitahara T, Takema Y (2008) Changes of human skin in subepidermal wound healing process. Skin research and technology: official journal of International Society for Bioengineering and the Skin 14: 436-439.

The invention claimed is:

1. A method for improving skin scar colour matching by reducing scar hyperpigmentation of a wound in a subject having or at risk of scar hyperpigmentation comprising administering a therapeutic amount of an agent that positively modulates β2-adrenergic receptor conformation, or receptor activity, or activation thereof, effective to reduce scar hyperpigmentation to said subject, wherein said wound is shielded from UV radiation, and wherein scar hyperpigmentation is reduced.

2. The method of claim 1, wherein the subject is selected as being at risk of hyperpigmentation on the basis of one or more of the following factors:
   (a) the subject has previously developed hyperpigmentation of a scar;
   (b) the subject tans readily on exposure to sunshine or ultraviolet (UV) radiation, rather than burning;
   (c) the subject has a non-Caucasian racial origin; or
   (d) the subject's skin colour is considered to be darker than that typical of a naturally fair-haired Caucasian person.

3. The method of claim 1, wherein the subject is selected as being at risk of hyperpigmentation because they are at least predominantly of Chinese, black African, Asian or Southern European racial origin, and/or if their skin type is Fitzpatrick Scale Type III, IV, V or VI.

4. The method of claim 1, wherein the agent that positively modulates β2-AR is a β2-adrenergic receptor agonist.

5. The method of claim 4, wherein the β2-adrenergic receptor agonist is one or more of Levosalbutamol, Isoproterenol ($\beta_1$ and ($\beta_2$), Metaproterenol, Terbutaline, Isoetarine, pirbuterol, procaterol, ritodrine, epinephrine, fenoterol, butoxamine, salbutamol, clenbuterol, formoterol, or salmeterol.

6. The method of claim 5, wherein the agent is Salbutamol.

7. The method of claim 1, wherein the wound is a penetrating wound or non-penetrating wound formed as a result of physical insult or injury iatragenesis or genetic susceptibility.

8. The method of claim 1, wherein the agent is administered topically or systemically.

9. The method of claim 1, wherein the agent is incorporated into a plaster, bandage, wound dressing or other occlusive, protective product used in standard wound care, or into a pharmaceutically acceptable transdermal patch, or into a gel of hydrocolloid or other suitable composition.

10. The method of claim 7, wherein said physical insult or injury comprises a graze, an abrasion, a surgical incision, a burn, or post-inflammatory hyperpigmentation.

11. The method of claim 10, wherein post-inflammatory hyperpigmentation results from eczema, psoriasis or acne.

12. The method of claim 1, wherein the skin colour of step (d) is defined in an area that is not tanned.

* * * * *